(12) United States Patent
Shannon et al.

(10) Patent No.: US 9,364,360 B2
(45) Date of Patent: Jun. 14, 2016

(54) CATHETER SYSTEMS AND METHODS FOR MANUFACTURE

(71) Applicant: Covidien LP, Mansfield, MA (US)

(72) Inventors: Donald Shannon, Trabuco Canyon, CA (US); Misty Coburn, Longmont, CO (US); Eric Rowson, Laguna Niguel, CA (US)

(73) Assignee: Covidien LP, Mansfield, MA (US)

( * ) Notice: Subject to any disclaimer, the term of this patent is extended or adjusted under 35 U.S.C. 154(b) by 91 days.

(21) Appl. No.: 14/174,077

(22) Filed: Feb. 6, 2014

(65) Prior Publication Data

US 2015/0216692 A1 Aug. 6, 2015

(51) Int. Cl.
| | |
|---|---|
| A61F 2/958 | (2013.01) |
| B32B 38/06 | (2006.01) |
| B32B 37/06 | (2006.01) |
| A61F 2/966 | (2013.01) |
| B29C 37/00 | (2006.01) |
| B29C 33/48 | (2006.01) |
| B29C 33/42 | (2006.01) |
| B29C 43/02 | (2006.01) |
| B29C 43/36 | (2006.01) |
| B29C 53/14 | (2006.01) |
| B29C 33/76 | (2006.01) |
| B32B 37/14 | (2006.01) |
| B32B 38/10 | (2006.01) |

(52) U.S. Cl.
CPC .................. *A61F 2/966* (2013.01); *B32B 38/06* (2013.01); *A61F 2002/9665* (2013.01); *B29C 33/42* (2013.01); *B29C 33/424* (2013.01); *B29C 33/48* (2013.01); *B29C 33/485* (2013.01); *B29C 33/76* (2013.01); *B29C 37/0003* (2013.01); *B29C 37/0017* (2013.01); *B29C 37/0021* (2013.01); *B29C 37/0053* (2013.01); *B29C 43/021* (2013.01); *B29C 53/14* (2013.01); *B29C 2043/023* (2013.01); *B29C 2043/024* (2013.01); *B29C 2043/025* (2013.01); *B29C 2043/3665* (2013.01); *B29C 2043/3668* (2013.01); *B32B 37/06* (2013.01); *B32B 37/14* (2013.01); *B32B 38/10* (2013.01)

(58) Field of Classification Search
None
See application file for complete search history.

(56) References Cited

U.S. PATENT DOCUMENTS

| | | | | |
|---|---|---|---|---|
| 5,244,619 | A | * | 9/1993 | Burnham .......... A61M 25/0012 264/171.2 |
| 5,681,296 | A | * | 10/1997 | Ishida ............... A61M 25/0009 600/585 |
| 5,704,926 | A | | 1/1998 | Sutton |
| 5,762,631 | A | * | 6/1998 | Klein ................ A61M 25/0021 264/171.12 |
| 6,016,848 | A | * | 1/2000 | Egres, Jr. .................. F16L 9/12 138/109 |
| 6,306,124 | B1 | | 10/2001 | Jones et al. |
| 6,503,353 | B1 | | 1/2003 | Peterson et al. |
| 7,018,372 | B2 | | 3/2006 | Casey et al. |
| 7,438,712 | B2 | | 10/2008 | Chouinard |
| 7,718,106 | B2 | | 5/2010 | Spencer et al. |

(Continued)

*Primary Examiner* — Jeffrey Wollschlager
(74) *Attorney, Agent, or Firm* — Elizabeth A. O'Brien, Esq.

(57) ABSTRACT

A method for manufacturing a catheter, includes forming a mandrel by arranging at least first and second elongate members in an at least partial longitudinal juxtaposed relation with respect to a longitudinal axis defined by the mandrel, mounting an inner liner having an internal surface about the mandrel, treating the inner liner whereby the first and second elongate members of the mandrel cause irregularities within the internal surface of the inner liner, positioning an outer member about the inner liner and removing at least the inner liner from the mandrel, thereby forming a catheter having the inner liner with irregularities.

15 Claims, 7 Drawing Sheets

(56) References Cited

U.S. PATENT DOCUMENTS

| | | | |
|---|---|---|---|
| 7,833,203 B2* | 11/2010 | Sherman | A61B 1/00075 600/139 |
| 7,993,384 B2* | 8/2011 | Wu | A61F 2/95 623/1.12 |
| 8,308,712 B2 | 11/2012 | Provost et al. | |
| 8,359,723 B2* | 1/2013 | Voss | A61M 25/0009 29/450 |
| 8,440,122 B2* | 5/2013 | Voss | A61M 25/0009 264/154 |
| 9,085,054 B2* | 7/2015 | Merk | B23P 11/00 |
| 2004/0143239 A1 | 7/2004 | Zhou et al. | |
| 2004/0176740 A1 | 9/2004 | Chouinard | |
| 2006/0155302 A1 | 7/2006 | Sisken et al. | |
| 2007/0078439 A1 | 4/2007 | Grandt et al. | |
| 2007/0208407 A1* | 9/2007 | Gerdts | A61F 2/95 623/1.11 |
| 2007/0250039 A1 | 10/2007 | Lobbins et al. | |
| 2008/0312639 A1 | 12/2008 | Weber | |
| 2010/0145429 A1* | 6/2010 | Dhoke | A61F 2/95 623/1.11 |
| 2010/0286791 A1 | 11/2010 | Goldsmith | |
| 2011/0238041 A1 | 9/2011 | Lim et al. | |
| 2012/0071822 A1 | 3/2012 | Romo et al. | |
| 2013/0006174 A1 | 1/2013 | Phan | |
| 2014/0173878 A1* | 6/2014 | Merk | B23P 11/00 29/446 |

\* cited by examiner

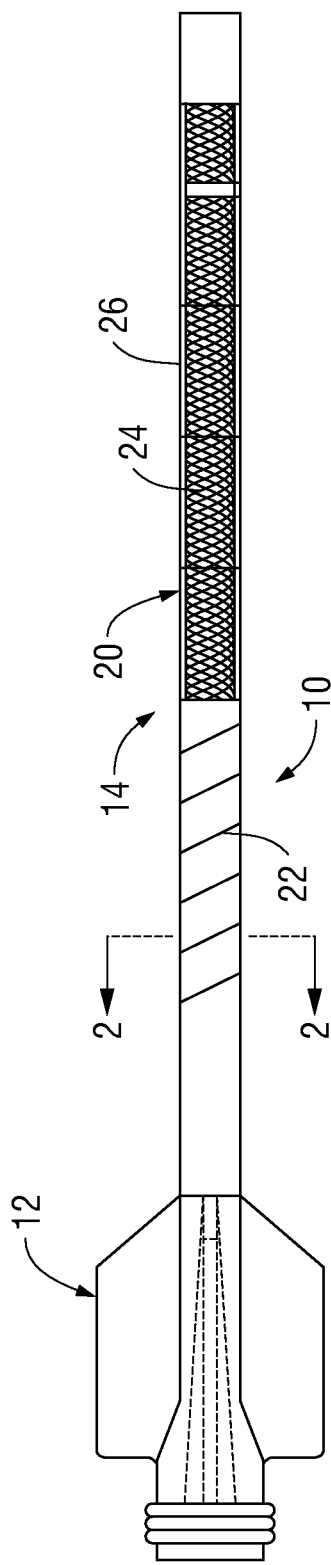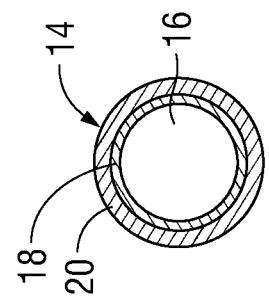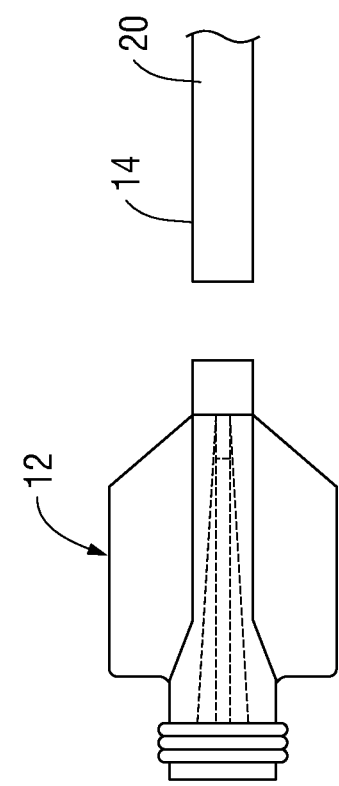

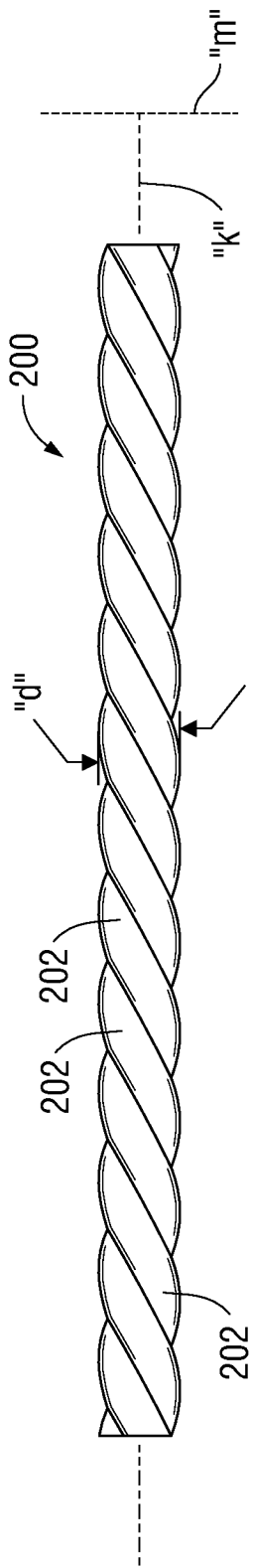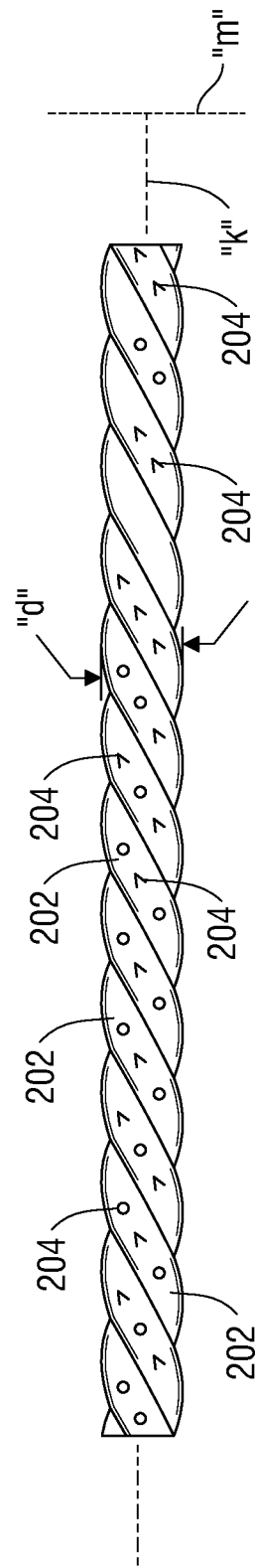

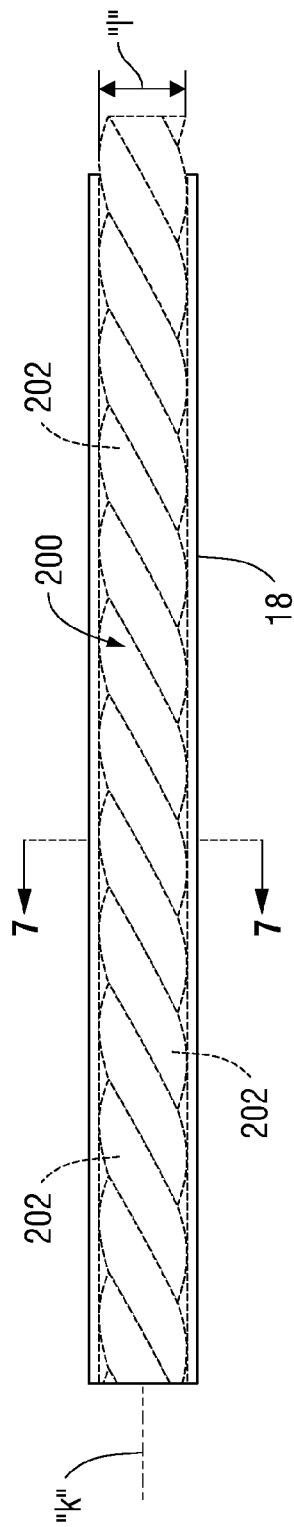
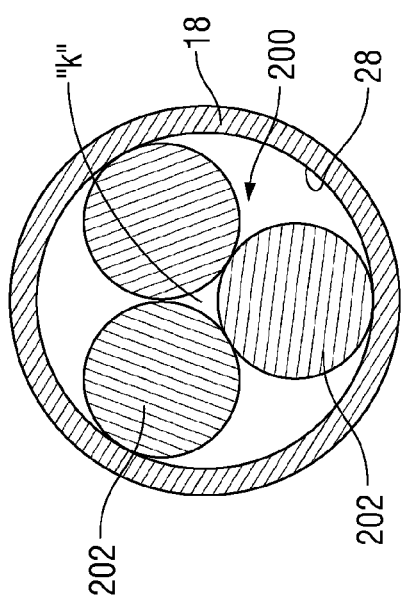
FIG. 6
FIG. 7

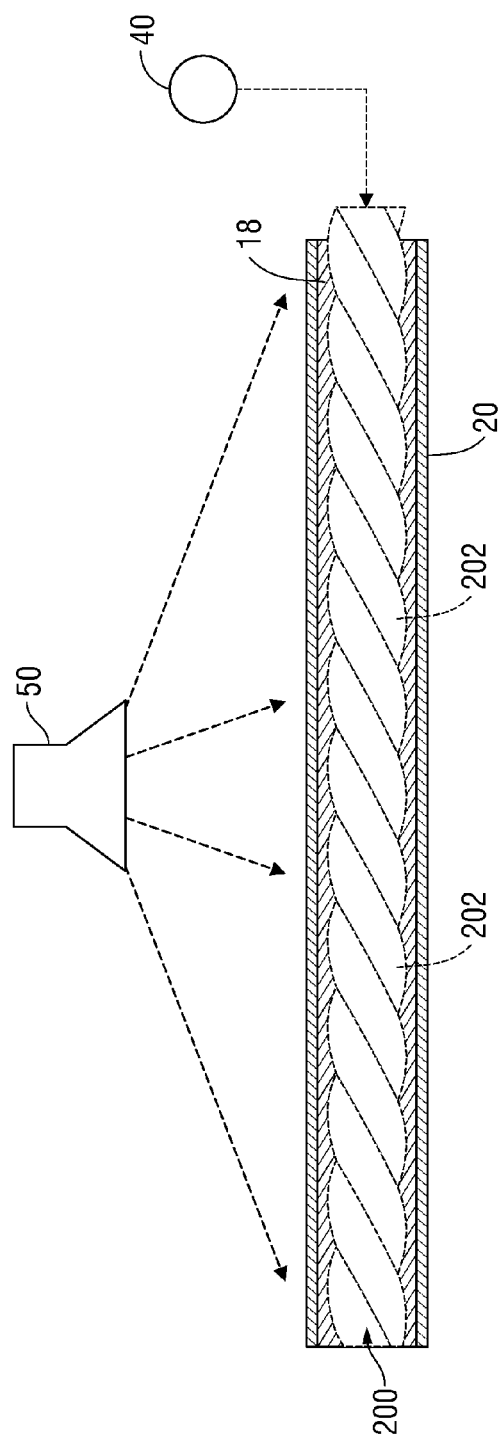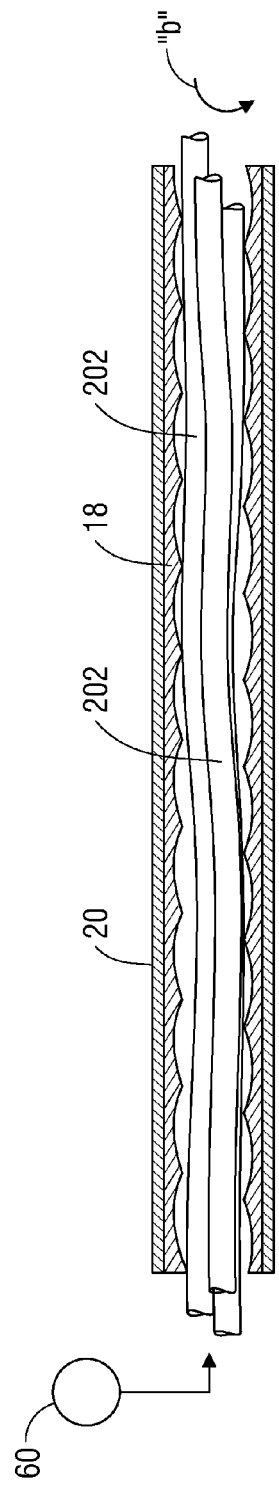
FIG. 8
FIG. 9

CATHETER SYSTEMS AND METHODS FOR MANUFACTURE

BACKGROUND

1. Technical Field

The present disclosure generally relates to catheters, and, in particular, relates to a method for manufacturing a catheter used in delivery of interventional medical devices.

2. Description of Related Art

Catheters are used in medical procedures to deliver interventional devices or implants to treatment sites. In the treatment of the neurovasculature, the clinician may use a microcatheter to navigate through the tortuous neurovasculature. A microcatheter provides a conduit through which various interventional devices may be introduced to treat a malformation within the neurovasculature. Exemplary interventional devices may include an intravascular stent, embolic coils, a flow diverter, a flow restoration device and/or a liquid embolic.

Catheters may also be components of delivery systems used to deliver stent. One typical stent delivery system includes a balloon catheter where the stent is positioned on the balloon of the catheter. The catheter is advanced within the vasculature to a targeted site and the balloon expanded to correspondingly expand the stent against the vessel wall. Another stent delivery system, for a self-expanding stent, may include inner and outer catheters. The stent is constrained within the outer catheter and advanced to the targeted site. The outer catheter is thereafter retracted, or the inner catheter advanced, to expose the stent, which self-expands, for application against the vessel wall.

When deploying interventional devices, resistance often occurs between the device and the inner surface of the catheter lumen. The generally smooth inner lumen of the catheter often increases resistance. Common methods of reducing resistance between the device and the lumen include lubricious coatings, catheter material selection, or the inclusion of an additional catheter lining. Another issue associated with catheter manufacture is the difficulty associated with assembly and disassembly of the catheter components relative to the mandrel(s) used in the process. In a typical process, various tubings, linings and/or coils to be incorporated within the catheter are positioned on one or more mandrels, and subjected to treatment such as application of thermal energy, e.g., to connect the components. However, subsequent to treatment, separation of the catheter components from the mandrel(s) often presents obstacles due to the reduction in the diameter of the innermost component adjacent the mandrel.

SUMMARY

Accordingly, the present disclosure is directed to an improved process for manufacturing a catheter. In accordance with an embodiment, a method for manufacturing a catheter, includes:

forming a mandrel by arranging at least first and second elongate members in an at least partial longitudinal juxtaposed relation with respect to a longitudinal axis defined by the mandrel;

mounting an inner liner having an internal surface about the mandrel;

treating the inner liner whereby the first and second elongate members of the mandrel cause irregularities within the internal surface of the inner liner;

positioning the outer member about the inner liner; and removing at least the inner liner from the mandrel, whereby a catheter is formed having the inner liner with irregularities.

In embodiments, forming the mandrel includes at least partially winding the first and second elongate members relative to each other and about the longitudinal axis. In some embodiments, removing the inner liner includes at least partially unwinding the first and second elongate members relative to each other and the longitudinal axis.

In other embodiments, removing the inner liner includes transitioning the mandrel from a first condition having a first effective cross-sectional dimension to a second condition having a second effective cross-sectional dimension less than the first cross-sectional dimension. The second cross-sectional dimension of the mandrel is less than an internal dimension defined by the internal surface of the inner liner subsequent to treating the inner liner.

In embodiments, treating the inner liner includes subjecting the inner liner to thermal energy to facilitate at least partial penetration of the first and second elongate members within the internal surface to assist in forming the surface irregularities. Subjecting the inner liner to thermal energy may include heating the mandrel.

In other embodiments, the method includes cooling the mandrel subsequent to heating the mandrel. At least partially unwinding the first and second elongate members may be performed subsequent to cooling the mandrel.

In some embodiments, positioning the outer member includes mounting the outer member over the inner liner when the inner liner is mounted about the mandrel. The method may include cooling the outer member during subjecting the inner liner to thermal energy.

In other embodiments, the inner liner includes polytetrafluoroethylene (PTFE) and wherein subjecting the inner liner to thermal energy includes heating the PTFE to increase a density of the PTFE. In some embodiments, the method includes mounting the outer member over the inner liner when the inner liner is mounted about the mandrel, and cooling the outer member during subjecting the inner liner to thermal energy.

In embodiments, forming the mandrel includes at least partially winding the first and second elongate members relative to each other and about the longitudinal axis to selectively control a longitudinal length of the mandrel.

In embodiments, the first and second elongate members include supplemental surface deformations. The surface deformations may be one of protrusions, curvatures or indentations, and wherein treating the inner liner causes supplemental irregularities in the inner surface of the inner liner generally corresponding to the one of the protrusions, curvatures or indentations.

In some embodiments, a method for manufacturing a catheter includes:

forming a mandrel by assembling at least first and second elongate members in an at least partial coiled or twisted assembled condition;

positioning a catheter about the mandrel, the catheter having an inner surface defining a lumen;

treating the catheter whereby the first and second elongate members cause irregularities within the internal surface of the catheter;

disassembling the mandrel; and removing the catheter relative to the mandrel.

In other embodiments, a mandrel for use in forming surface irregularities within an inner surface of a catheter is provided. The mandrel includes first and second elongate members defining a longitudinal axis. The first and second elongate members have a first at least partially wound condition, and a second at least partially unwound condition. The first and second elongate members are dimensioned to support a catheter during treatment thereof when in the first condition, and capable of being moved to the second condition subsequent to treatment of the catheter to facilitate removal of the catheter relative to the mandrel.

In embodiments, the first and second elongate members define a first effective cross-sectional dimension when in the first condition thereof and define a second effective cross-sectional dimension when in the second condition thereof where the second cross-sectional dimension is less than the first cross-sectional dimension.

In other embodiments, an implant delivery system includes a catheter defining a longitudinal axis and having an inner surface with surface irregularities and an implant member disposed within the longitudinal lumen of the catheter. The implant member is longitudinally movable within the longitudinal lumen whereby the irregularities of the inner surface reduce friction between the implant member and the inner surface. The implant member is adapted to transition from an initial constrained condition within the longitudinal lumen to an actuated expanded condition upon deployment from the catheter. In embodiments, the implant member is a stent. In other embodiments, an inner shaft is disposed within the longitudinal lumen. The inner shaft and the catheter may be adapted for relative longitudinal movement whereby the inner shaft is engageable with the implant member to deploy the implant member from the catheter.

Embodiments can include one or more of the following advantages. The mandrel described herein forms irregular surfaces on the inner liner or the inner surface of the catheter. These irregular surfaces advantageously reduce surface contact area with an interventional device introduced through the catheter thereby minimizing friction between the components, which, promotes delivery and/or resheathing of the interventional device. The mandrel also may be disassembled during the manufacturing process thereby facilitating removal of the mandrel relative to the inner liner and the catheter.

Other aspects, features, and advantages will be apparent from the description, drawings, and the claims.

BRIEF DESCRIPTION OF THE DRAWINGS

Embodiments of the present disclosure will be readily appreciated by reference to the drawings wherein:

FIG. 1 illustrates a side elevation view with portions removed of an exemplary catheter assembly, including a catheter hub and an elongate catheter manufactured in accordance with the principles of the present disclosure;

FIG. 2 is a cross-sectional view of the catheter taken along the lines 2-2 of FIG. 1;

FIG. 4 is a side plan view of a mandrel utilized in the method of manufacture of the catheter;

FIG. 5 is a side plan view of an embodiment of the mandrel including supplemental surface irregularities;

FIG. 6 is a side plan view of the inner liner positioned about the mandrel with the mandrel in phantom;

FIG. 7 is a cross-sectional view taken along the lines 7-7 of FIG. 6;

FIG. 8 is a side cross-sectional view illustrating an outer member positioned about the inner liner during treatment of the inner liner, and with the mandrel depicted in phantom;

FIG. 9 is a side cross-sectional view similar to the view of FIG. 8 illustrating the mandrel disassembled;

FIG. 11 is a perspective view illustrating the catheter of FIG. 10 coupling to a catheter hub;

DETAILED DESCRIPTION

Figure 3:
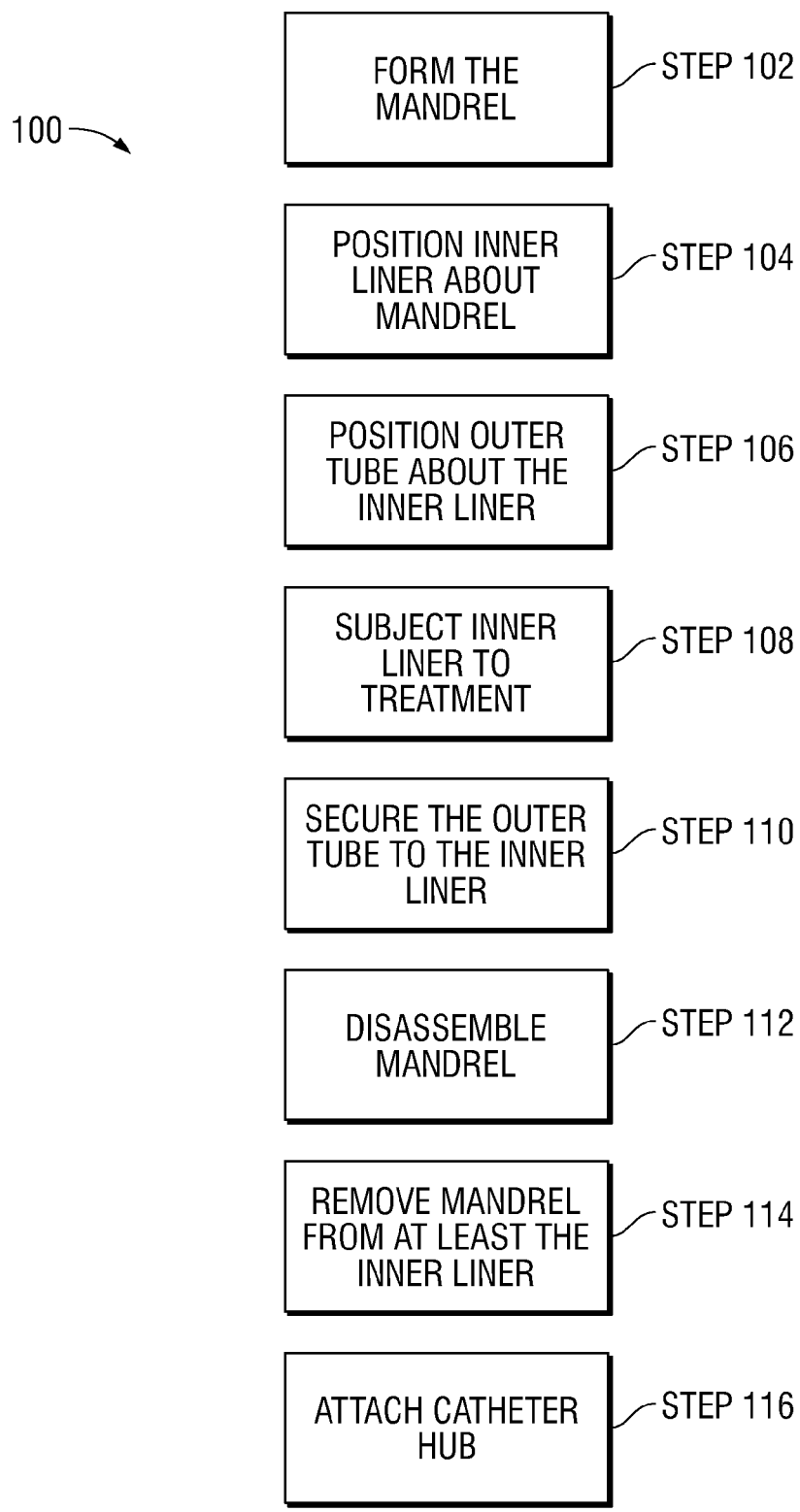
FIG. 3 is a flow chart illustrating the sequence of steps in the method of manufacture of the catheter.

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure. Like reference numerals may refer to similar or identical elements throughout the description of the figures.

The present disclosure relates to a method or process of manufacturing a catheter, and a mandrel for use in forming the catheter in accordance with the method. The manufactured catheter may be a component of a catheter assembly, and coupled to a catheter hub. For example, the catheter may be a component of a catheter assembly having particular application in a neurovascular procedure, e.g., a microcatheter assembly, for the delivery and/or retrieval of neurovascular interventional devices. In embodiments, the catheter may be a component of an assembly for use in any interventional, diagnostic, and/or therapeutic procedure including coronary vascular, peripheral vascular and gastro-intestinal applications in addition to neurovascular applications.

In the following description, the term "catheter" is to include the elongated body segment of a catheter assembly, which may or may not be coupled to a catheter hub. The catheter is at least partially positionable within the body, e.g., the neurovasculature of the subject.

FIGS. 1-2 illustrate an exemplary catheter which may be manufactured in accordance with the principals of the present disclosure. The catheter, in this embodiment, is a component of a microcatheter assembly for delivering an interventional device in the neurovascular space. The microcatheter assembly 10 includes a housing or catheter hub 12 and an elongated catheter 14 extending from the catheter hub 12. The catheter 14 may define a longitudinal lumen 16 (shown in FIG. 2) extending the length of the catheter 14. The catheter 14 may include multiple components assembled together to form the catheter 14 or may be a single tube component. In embodiments, the catheter 14 includes an inner liner 18 which extends along at least a portion of the length of the catheter 14 and defines the longitudinal lumen 16, and an outer member 20 positioned about the inner liner 18. The outer member 20 may be a single tube or include multiple components. In the exemplary microcatheter assembly 10 described herein, the outer member 20 includes a hypotube 22 positioned over at least the proximal end segment of the inner liner 18 and a braid 24 positioned over at least the distal end segment of the inner liner 18. The hypotube 22 may be fabricated from a stainless steel or a reinforced polymer and the braid 24 may be fabricated from nitinol. An outer jacket 26 may be positioned over or embedded in the braid 24 and the hypotube 22. Other arrangements for the outer member 20 are also envisioned.

Additionally, or alternatively, the catheter 14 may include some of the structural features of the commercially available microcatheters such as the Orion™, Echelon™, Marathon™, and Nautica™ microcatheters sold by Covidien LP, Irvine, Calif. In other embodiments, the manufactured catheter may be a component of a catheter having application in any of the fields mentioned hereinabove.

Referring now to FIG. 3, a flow chart illustrating one exemplary method or process 100 for manufacturing, e.g., the catheter 14 of FIGS. 1-2, is illustrated. The first step in the process 100 is to form or provide a mandrel. (Step 102). FIG. 4 illustrates one mandrel 200 for use in the process 100 of manufacture of the catheter. The mandrel 200 includes a plurality of elongate members 202, such as wires, filaments, or strands, which are assembled together to define the combined orientation depicted in FIG. 4. The combined orientation may be inclusive of a variety of configurations of the elongate members 202, including, e.g., twisted, coiled, interwoven, curved, bent, side by side, juxtaposed or any other arrangement in which the elongate members 202 cooperate to define a cross-sectional dimension or diameter suitable for the manufacture or assembly process. In one embodiment, three elongate members 202 are coiled or twisted upon each other to define the twisted configuration depicted in FIG. 4. However, the mandrel 200 may include two elongate members 202 or four or more elongate members 202. In one exemplary embodiment, the mandrel 200 defines a longitudinal axis "k" about which the elongate members 202 are twisted or arranged. Any suitable mechanisms for twisting the elongate members 202 may be utilized including mechanical systems or via manual manipulation. The twisted or assembled mandrel 200 defines an effective cross-sectional dimension or diameter "d" along orthogonal axis "m". The cross-sectional dimension "d" may approximate the internal diameter of the first tubing, lining or coil positioned about the mandrel during manufacture. The length of the mandrel 200 may be predetermined and dependent, at least in part to the lengths of the elongate members 202, and the respective pitch of the wound components.

The individual elongate members 202 forming the mandrel 200 may be fabricated from a metallic material. Suitable metallic materials include stainless steel, copper, silver-plated copper, brass, aluminum or any other material which may be deformed to assume any of the aforementioned combined configurations, and also be manipulated or deformed to assume an original configuration, e.g., a generally linear configuration. The elongate members 202 may also be adapted to conduct heat. In the alternative, the elongate members may be fabricated from a polymeric material such as polytetrafluoroethylene (PTFE) or a polyether ether ketone (PEEK). The choice of material for the elongate members 202 may be dependent on the desired shapes or surfaces to be imparted on the inner liner 18 or innermost surface of the catheter 14, and may be appropriately suited to withstand, without deformation, any chemical, thermal, or mechanical processing.

The elongate members 202 may be the same diameter or cross-section or alternatively have different cross-sections. The elongate members 202 each may include multiple component or strands, or be a single component. Various shapes for the elongate members 202 are contemplated including, e.g., circular, rectangular or oval in cross-section.

FIG. 5 illustrates one embodiment of a mandrel 200 where the elongate members 202 including additional supplemental surface irregularities such as pitted surfaces, bumps or protrusions and/or etched surfaces, designated as reference numeral 204, disposed on the outer surface of the elongate members 202, the significance of which will be appreciated from the discussion hereinbelow.

With reference now to FIGS. 6-7, in conjunction with FIG. 3, the process 100 is continued by positioning the inner liner 18 about the mandrel 200. (Step 104) The inner liner 18 may be fabricated from polytetrafluoroethylene (PTFE) or high-density polyethylene (HDPE). The inner liner 18 is generally tubular having an inner surface 28, and may define an internal diameter "l" generally approximating the effective cross-sectional dimension "d" (FIG. 4) of the mandrel 200. The inner liner 18 may be the innermost component of the catheter 14. In embodiments, the inner liner 18 may be fabricated from a material, which deforms, contracts or shrinks when subject to energy.

With reference to FIG. 8, in conjunction with FIG. 3, the process 100 may be continued by positioning the outer member 20 over the inner liner 18. (Step 106) The outer member 20 may be an outer tube fabricated from a material including, but not limited to, polymeric materials, elastomeric materials, for example, silicone and fabric materials, or a synthetic resin, for example, polyurethane, polyethylene, polypropylene, nylons, polytetrafluoroethylene (PTFE), polyether ether ketone (PEEK), PEBAX®, or polyimide. In embodiments, the outer member 20 includes a more dense material than the material of fabrication of the inner liner 18. It is further envisioned that the outer member 20 may include multiple tubes 20 which may be positioned over the inner liner 18. Alternatively, the outer member 20 may include the hypotube 22, braid 24 and the outer jacket 26 as discussed hereinabove.

With continued reference to FIGS. 3 and 8, the process 100 is continued by subjecting at least the inner liner 18 mounted about the mandrel 200 to treatment (Step 108). The treatment may include application of energy, identified schematically as reference numeral 40, to one or more of the elongate members 202 of the mandrel 200 which is then conveyed through the heat conducting material of the elongate members 202 to the inner liner 18. The energy source may be a laser, a heat lamp, a hot air applicator, a mechanical oscillator, an ultrasonic transducer, radio-frequency energy and/or any suitable heat source 40 capable of transferring mechanical energy or heat energy through, e.g., conduction, convection or radiation. During application of energy to the mandrel 200 and the inner liner 18, the outer member 20 may be cooled, e.g., with a cold air blower, depicted schematically as reference numeral 50. Alternatively, heat energy may be applied to the outer member 20, which is conveyed to the inner liner 18. In embodiments, the outer member 20 may be cooled as discussed hereinabove. The type of energy used and the temperature ranges applied to the elongate members 202 will be dependent on the material selection of the elongate members 202 and the materials of fabrication of the inner liner 18 and the outer member 20.

As a result of the treatment, e.g., the thermal treatment of Step 108, the inner liner 18 generally conforms, or at least partially conforms, to the outer boundary of the mandrel 200 and, thus, at least includes curved and/or disjoined surfaces generally corresponding to the outer curved, intersecting surfaces of the twisted elongate members 202 of the mandrel 200. In addition, with regard to the embodiment of the mandrel of FIG. 5, the supplemental or additional surface irregularities 204 on the elongate members 202 will impart corresponding additional irregularities to the inner surface 28 of the inner liner 18 in addition to the outer curved, intersecting surfaces. As will be discussed, these curved, intersecting and/or irregularities reduce friction within the inner liner 18 relative to an implant, which may pass through or otherwise be introduced through the inner liner 18 of the catheter 14, by reducing the surface area of contact with the inner liner 18.

In addition, the material of the inner liner 18 has a higher density subsequent to thermal treatment of Step 108. The higher dense, e.g., PTFE material, may also reduce friction forces with the implant and/or facilitate removal of the inner liner 18 from the mandrel 200. The outer member 20, which is subject to cooling, may not undergo any substantial deformation during the thermal treatment of Step 108.

The outer member 20 (with or without the hypotube 22, braid 24 and the outer jacket 26 if present) may be secured about the inner liner 18 (Step 110). Any known techniques including adhesives, bonding with or without thermal application may be applied to connect the outer member 20 and the inner liner 18.

With reference to FIG. 9, in conjunction with the flow chart of FIG. 3, once the outer member 20 is connected to the inner liner 18, the mandrel 200 may be disassembled to facilitate removal of the assembled components from the mandrel 200. (Step 112). In embodiments, the mandrel 200 may be cooled through a variety of mechanisms including, e.g., application of cold air, depicted schematically as reference numeral 60, to the elongate members 202 of the mandrel 200 or about the outer member 20. Once cooled, the elongate members 202 are disassembled or untwisted to assume the disjoined and substantially linear configuration depicted in FIG. 9. Disassembly may be affected through rotation of at least one end of the mandrel 200 in the direction of directional arrows "b" thereby delaminating or releasing the inner liner 18 relative to the elongate members 202 of the mandrel 200. In the disassembled condition, the effective cross-sectional dimension of the mandrel 200 may be less than the internal diameter of the inner liner 18.

Thereafter, the elongated members 202 of the mandrel 200 may be removed either individually, or in combination, from the inner liner 18 and the outer member 20. (Step 114). In embodiments, the elongated members 202 may be coated with silicon or other friction reducing material to facilitate removal from the inner liner 18. Alternatively, the inner liner 18 and the outer member 20 may be removed by sliding the components off the disassembled elongated members 202 of the mandrel 200.

Figure 10:
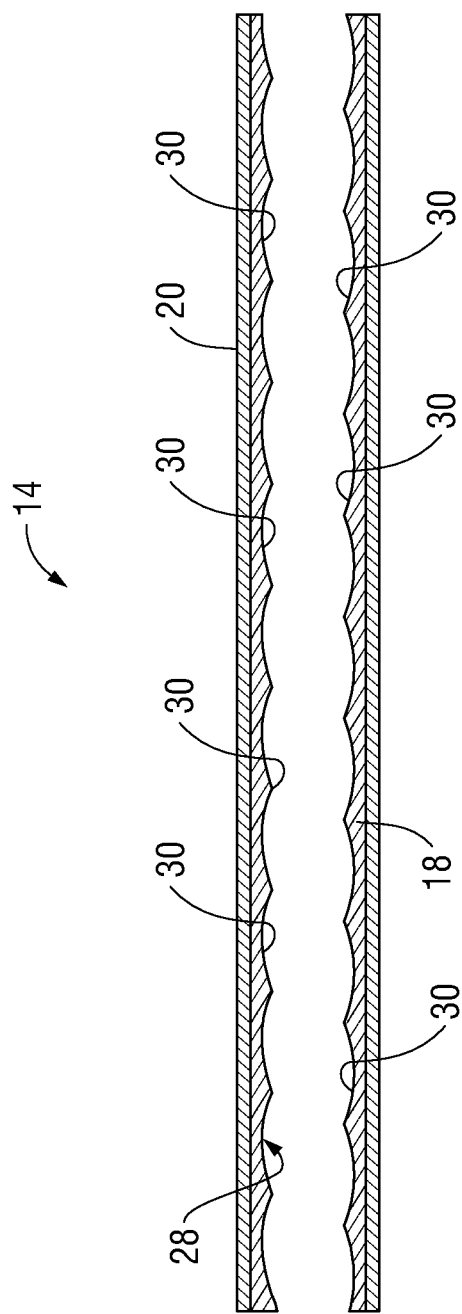
FIG. 10 is a side cross-sectional view of the catheter manufactured in accordance with the method incorporating the outer member and the inner liner, and illustrating the surface irregularities within the inner surface of the inner liner.

FIG. 10 illustrates the formed catheter 14, which includes the inner liner 18 and the connected outer member 20. The inner liner 18 has the inner surface 28 with surface irregularities 30. The surface irregularities 30 may be curved, intersecting and/or disjoined generally corresponding to the outer curved, intersecting surfaces of the twisted elongate members 202 of the mandrel 200. The inner surface 28 also may include other or additional surface irregularities corresponding to any other irregularities, which may be present on the outer surfaces of the elongate members 202 such as, e.g., those provided by the supplemental surface irregularities 204 on the elongate members 202 of the embodiment of FIG. 5.

Referring to FIG. 11, in conjunction with FIG. 3, the process may be continued by coupling the catheter tube 14 to the catheter hub 12 using known techniques. (Step 116). Thereafter, the catheter 14 may be utilized in a variety of intraluminal or intravascular procedures, e.g., in a neurovascular procedure for delivering an interventional treatment element such as a stent, a coil, a flow diverter, a flow restoration element, a thrombectomy element, a retrieval element, an aspirator or a snare. The reduced surface area provided by the surface irregularities 30 will reduce friction between the inner liner 18 and the interventional treatment element. The reduced friction will facilitate deployment of the treatment element and also enhance resheathing of the treatment element, if required, during the procedure.

Figure 12:
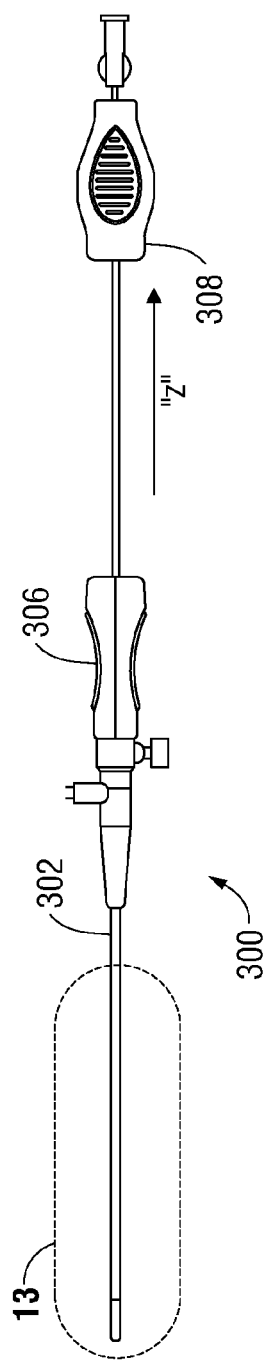
FIG. 12 is a side plan view of a stent delivery system incorporating the catheter.
Figure 13:
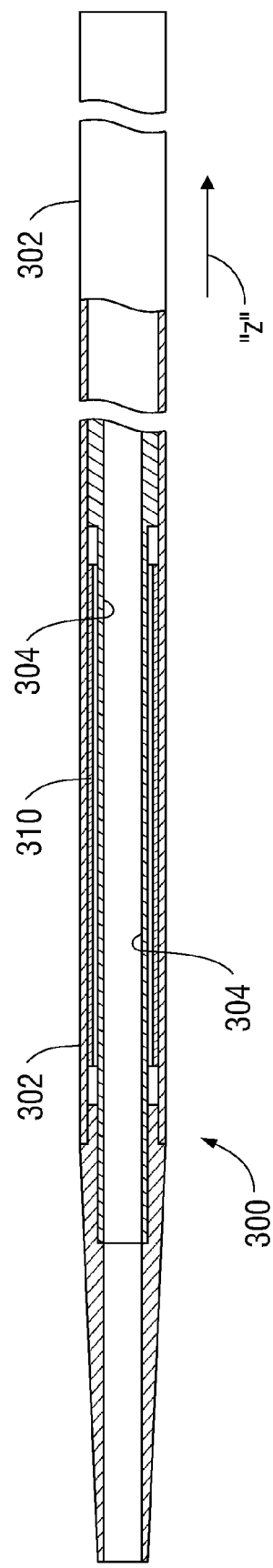
FIG. 13 is an enlarged view of the area of isolation depicted in FIG. 12.

FIGS. 12-13 illustrate the catheter member 14, formed in accordance with the above process, as a component of a stent delivery system 300. The stent delivery system 300 includes an outer catheter member 302 formed in accordance with the aforementioned process and an inner member 304 disposed within the catheter member 302. The catheter member 302 is connected to a handle 306 and the inner member 304 is connected to a housing 308. A stent 310 (schematically shown in FIG. 13) may be a self-expanding, open-celled, tubular stent and formed of a self-expanding, shape-memory or superelastic metal such as nitinol, or the like. The stent 310 may also be a self-expanding coil stent or any other self-expanding stent.

The stent 310 is carried on the stent delivery system 300 in a collapsed (or reduced diameter) state. Upon release of the stent 310 from the stent delivery system 300 (as will be described), the stent 310 expands to an enlarged diameter to abut against the walls of the patient's lumen in order to support patency of the lumen. In embodiments, the stent 310 engages the distal end of the inner member 304.

To deploy the stent 310, the handle 306 is moved in a proximal direction to retract the catheter member 302 in direction "z". The catheter member 302 slides over the stent 310, facilitated by the irregular surfaces 30 within the inner liner 18, which reduces the surface contact area of the stent 310 with the inner liner 18, to expose the stent 310. The stent 310 self-expands and is deployed within the body lumen, e.g., the vasculature of the subject.

The presence of any additional irregularities may further reduce friction between the implant and the inner surface 28 of the inner liner 18.

The above description and the drawings are provided for the purpose of describing embodiments of the present disclosure and are not intended to limit the scope of the disclosure in any way. For example, the inner liner 18 may be a component of the outer member 20 prior to mounting about the mandrel 200. Alternatively, the outer member 20 may be devoid of an inner liner 18 whereby the inner surface of the outer member 20 is subjected to the aforedescribed process to form irregularities in the inner surface of the outer member 20. As discussed, the outer member 20 may be a single tube or sleeve. The outer member 20 may be mounted about and connected to the inner liner 18 subsequent to positioning, treatment and removal of the inner liner 18 about the mandrel 200. The method or process steps may be combined or be in a different sequence. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A method for manufacturing a catheter, the method comprising:
   mounting an inner liner having an internal surface about a mandrel, the mandrel comprising first and second elongate members each at least partially wound relative to each other and about a longitudinal axis defined by the mandrel;
   treating the inner liner whereby the first and second elongate members of the mandrel cause irregularities within the internal surface of the inner liner;
   positioning an outer member about the inner liner; and removing at least the inner liner from the mandrel, wherein removing the inner liner includes at least partially unwinding the first and second elongate members relative to each other and the longitudinal axis, wherein a catheter is formed having the inner liner with irregularities.

2. The method according to claim 1, further comprising forming the mandrel by at least partially winding the first and second elongate members relative to each other and about the longitudinal axis.

3. The method according to claim 1 wherein removing the inner liner includes transitioning the mandrel from a first condition having a first effective cross-sectional dimension to a second condition having a second effective cross-sectional dimension less than the first cross-sectional dimension, the second cross-sectional dimension of the mandrel being less than an internal dimension defined by the internal surface of the inner liner subsequent to treating the inner liner.

4. The method according to claim 1 wherein treating the inner liner includes subjecting the inner liner to thermal energy to facilitate at least partial penetration of the first and second elongate members within the internal surface to assist in forming the surface irregularities.

5. The method according to claim 4 wherein subjecting the inner liner to thermal energy includes heating the mandrel.

6. The method according to claim 5 including cooling the mandrel subsequent to heating the mandrel.

7. The method according to claim 6 wherein at least partially unwinding the first and second elongate members is performed subsequent to cooling the mandrel.

8. The method according to claim 4 wherein positioning the outer member includes mounting the outer member over the inner liner when the inner liner is mounted about the mandrel.

9. The method according to claim 8 including cooling the outer member during subjecting the inner liner to thermal energy.

10. The method according to claim 4 wherein the inner liner includes polytetrafluoroethylene (PTFE) and wherein subjecting the inner liner to thermal energy includes heating the PTFE to increase a density of the PTFE.

11. The method according to claim 10 including mounting the outer member over the inner liner when the inner liner is mounted about the mandrel and cooling the outer member during subjecting the inner liner to thermal energy.

12. The method according to claim 2 wherein forming the mandrel includes at least partially winding the first and second elongate members relative to each other and about the longitudinal axis to selectively control a longitudinal length of the mandrel.

13. The method according to claim 1 wherein the first and second elongate members include supplemental surface deformations, the supplemental surface deformations being one of protrusions, curvatures or indentations, and wherein treating the inner liner causes supplemental irregularities in the inner surface of the inner liner generally corresponding to the one of the protrusions, curvatures or indentations.

14. A method for manufacturing a catheter, the method including:
    positioning a catheter about a mandrel, the catheter having an inner surface defining a lumen, the mandrel comprising at least first and second elongate members in an at least partial coiled or twisted assembled condition;
    treating the catheter whereby the first and second elongate members cause irregularities within the internal surface of the catheter;
    disassembling the mandrel, wherein disassembling the mandrel includes at least partially unwinding the first and second elongate members from the at least partial coiled or twisted assembled condition; and
    removing the catheter relative to the mandrel.

15. The method according to claim 1, further comprising forming the mandrel by at least arranging the at least first and second elongate members in an at least partial longitudinal juxtaposed relation with respect to a longitudinal axis defined by the mandrel.

* * * * *